(12) United States Patent
Puentener et al.

(10) Patent No.: US 8,450,496 B2
(45) Date of Patent: May 28, 2013

(54) PROCESS FOR THE PREPARATION OF PROPIONIC ACID DERIVATIVES

(75) Inventors: Kurt Puentener, Basel (CH); Michelangelo Scalone, Birsfelden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 282 days.

(21) Appl. No.: 12/725,480

(22) Filed: Mar. 17, 2010

(65) Prior Publication Data

US 2010/0249428 A1 Sep. 30, 2010

(30) Foreign Application Priority Data

Mar. 24, 2009 (EP) .................................... 09156074
Dec. 7, 2009 (EP) .................................... 09178220

(51) Int. Cl.
 *C07D 263/36* (2006.01)
(52) U.S. Cl.
 USPC ........................................................ 548/236
(58) Field of Classification Search
 None
 See application file for complete search history.

(56) References Cited

U.S. PATENT DOCUMENTS

| | | | |
|---|---|---|---|
| 5,466,844 A | 11/1995 | Spindler et al. | |
| 7,262,303 B2 | 8/2007 | Puentener et al. | |
| 7,365,207 B2 | 4/2008 | Puentener et al. | |
| 2011/0118472 A1 * | 5/2011 | Zhou et al. | 548/101 |

FOREIGN PATENT DOCUMENTS

| | | | |
|---|---|---|---|
| CN | 100432083 | * | 11/2008 |
| EP | 0564406 | | 10/1993 |
| EP | 0612758 | | 8/1994 |
| EP | 2272853 | | 1/2011 |
| WO | 02092084 | | 11/2002 |
| WO | 2005/030764 | | 4/2005 |
| WO | WO 2005/030764 | * | 4/2005 |
| WO | WO 2009/129700 | * | 10/2009 |
| WO | 2010/108861 | | 9/2010 |

OTHER PUBLICATIONS

Li et al. JACS (2008), 130, pp. 8594-8595.*
Machine translation of CN 100432083, obtained from <http://cs.dialog.com/client/csc_sh127/> Accessed Jul. 11, 2012.*
Human translation of CN 100432083 (pp. 8-9). STIC Translations Branch. Obtained Jul. 12, 2012.*
Chen, W. et al, Stereoselective synthesis of ferrocene-based C2-symmetric diphosphine ligands: Application to the highly enantioselective . . . , Angewandte Chemie, (2007() 46:22 4141-4144 XP009100217.
Spindler F et al, Tetrahedron Asymmetry, "Modular chiral ligands: the profiling of the Mandyphos and . . ." (2004) 15:14 2299-2306 XP004523722.
Zhou et al., JACS, vol. 130 pp. 8584-8585 (2008).
Herde et al., Inorg. Syn. pp. 18-20 (1974).
Green et al., J. Chem. Soc. pp. 2334-2337 (1971).
McCormack et al., Angew. Chem. Int. Ed. vol. 46, pp. 4141-4144 (2007).
Briel et al., Catalysis of Organic Reactions, vol. 123, CRC Press, Boca Raton, pp. 203-210 (2009).
Li Shen et al., Journal of the American Chemical Society (XP002580008), 130(27):8584-8585 (Jul. 9, 2008).
Zhu, S-F et al., Journal of the American Chemical Society (XP002627321), 128(39):12886-12891 (Oct. 4, 2006).
(International Search Report PCT/EP2011/051610 Mar. 18, 2011).
(Taiwanese Search Report in Corres Appl 099108411 Nov. 8, 2012).

* cited by examiner

*Primary Examiner* — Rebecca Anderson
*Assistant Examiner* — Alicia L Otton
(74) *Attorney, Agent, or Firm* — Robert C. Hall

(57) ABSTRACT

The invention relates to a process for the preparation of a compound of formula (I)

(I)

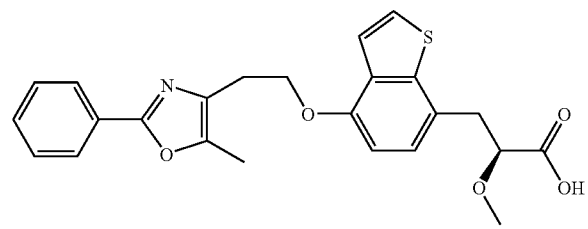

or a salt thereof.

3 Claims, No Drawings

PROCESS FOR THE PREPARATION OF PROPIONIC ACID DERIVATIVES

PRIORITY TO RELATED APPLICATION(S)

This application claims the benefit of European Patent Application No. 09156074.8, filed Mar. 24, 2009, and of European Patent Application No. 09178220.1, filed Dec. 7, 2009, both of which are hereby incorporated by reference in its entirety.

FIELD OF THE INVENTION

The present invention is concerned with a novel process for the preparation of (S)-2-methoxy-3-{4-[2-(5-methyl-2-phenyl-oxazol-4-yl)-ethoxy]-benzo[b]thiophen-7-yl}-propionic acid or a salt thereof.

The invention relates in particular to a process for the preparation of a compound of formula (I)

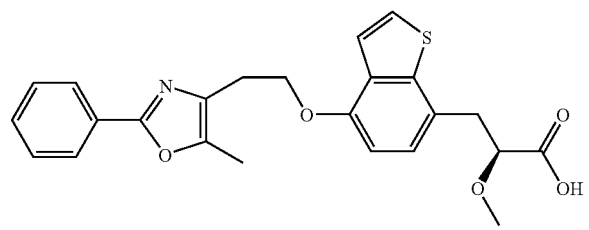

(I)

or a salt thereof, wherein a compound of formula (II)

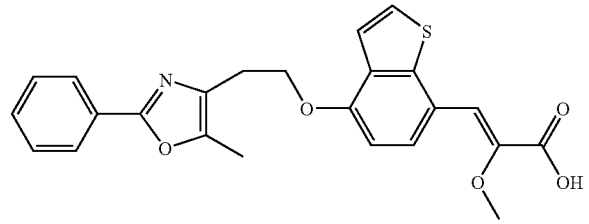

(II)

or a salt thereof is hydrogenated
(a) in the presence of a catalyst comprising iridium; or
(b) in the presence of a catalyst comprising ruthenium and a compound of: formula (IV),

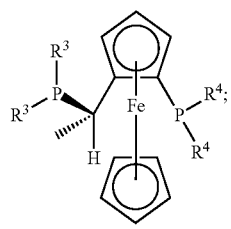

(IV)

formula (V),

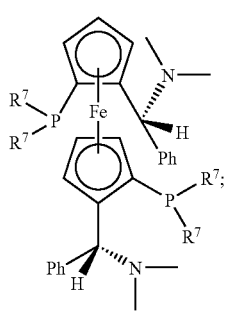

(V)

formula (VI),

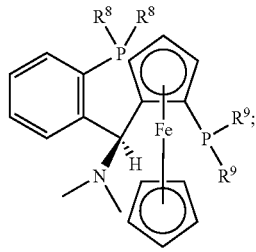

(VI)

or formula (VII),

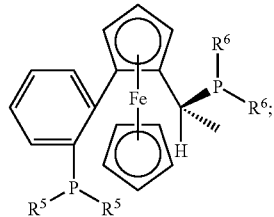

(VII)

wherein
$R^3$ is alkyl, cycloalkyl or aryl;
$R^4$ is cycloalkyl, aryl or heteroaryl;
$R^5$ is cycloalkyl or aryl;
$R^6$ is cycloalkyl or aryl;
$R^7$ is cycloalkyl or aryl;
$R^8$ is cycloalkyl or aryl; and
$R^9$ is cycloalkyl or aryl.

BACKGROUND OF THE INVENTION

The compound of formula (I) is known in the art and is described for example in international application WO 02/092084. It is especially useful for the prophylaxis and/or treatment of diabetes mellitus type I and II.

The process according to the invention allows the synthesis of the compound of formula (I) with high enantiomeric excess. It can be performed in dichloromethane and the use of complex solvent mixtures can be avoided. The process with the catalyst comprising iridium gives particularly high yield and high enantiomeric excess of the compound of formula (I).

Furthermore, optically pure compound of formula (I) is obtained without the use of multiple crystallization of diastereomeric salts.

SUMMARY OF THE INVENTION

The present invention relates to a process for the preparation of a compound of formula (I)

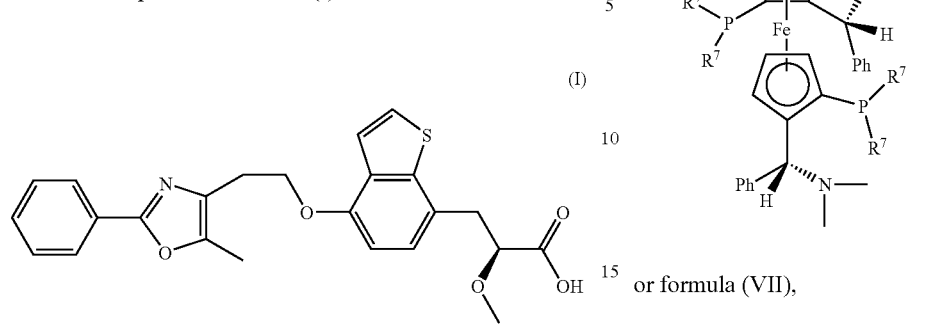

(I)

or a salt thereof, wherein a compound of formula (II)

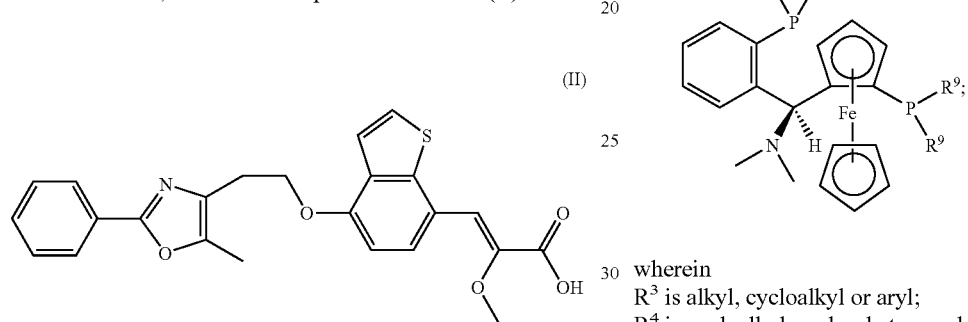

(II)

or a salt thereof is hydrogenated (a) in the presence of a catalyst comprising iridium; or
(b) in the presence of a catalyst comprising ruthenium and a compound of: formula (IV),

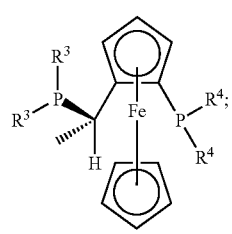

(IV)

formula (V),

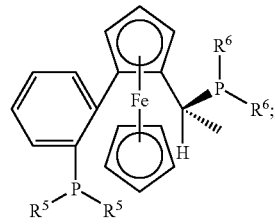

(V)

formula (VI), (VI)

(VII)

or formula (VII), wherein
$R^3$ is alkyl, cycloalkyl or aryl;
$R^4$ is cycloalkyl, aryl or heteroaryl;
$R^5$ is cycloalkyl or aryl;
$R^6$ is cycloalkyl or aryl;
$R^7$ is cycloalkyl or aryl;
$R^8$ is cycloalkyl or aryl; and
$R^9$ is cycloalkyl or aryl.

The present invention relates also to a compound of formula (I) or a salt thereof obtained using the above process.

DETAILED DESCRIPTION OF THE INVENTION

The term "catalyst" refers to a complex of ruthenium or iridium respectively with a chiral ligand. In such ruthenium complexes, ruthenium is preferably characterised by the oxidation number II. In such iridium complexes, iridium is preferably characterized by the oxidation number I.

The term "alkyl" refers to a branched or straight chain monovalent alkyl radical of one to eight carbon atoms, preferably one to four carbon atoms. This term is further exemplified by such radicals as methyl, ethyl, n-propyl, iso-propyl, iso-butyl, n-butyl, tert-butyl and the like with methyl, tert-butyl and iso-propyl being preferred.

The term "alkoxy" refers to the group alkyl-O—. A preferred alkoxy group is methoxy.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl. Cyclohexyl is a preferred cycloalkyl.

The term "aryl" relates to the phenyl or naphthyl group, preferably the phenyl group, which can optionally be mono- or multiply-substituted, particularly mono-, di- or tri-substituted by halogen, hydroxy, CN, $CF_3$, $NO_2$, $NH_2$, N(H, alkyl), $N(alkyl)_2$, carboxy, aminocarbonyl, alkyl, alkoxy, phenyl and/or phenyloxy. Preferred substituents are halogen, alkyl, $CF_3$ and alkoxy, particularly alkyl, $CF_3$ and alkoxy.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can comprise 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl". Preferred heteroaryl groups are 2-thienyl and 2-furyl. 2-Furyl is particularly preferred.

The term "halide" refers to a halogen atom bearing a negative charge such as fluoride, chloride, bromide and iodide.

The term "pharmaceutically acceptable salts" embraces salts of the compound of formula (I) with pharmaceutically acceptable bases such as alkali salts, e.g. Na- and K-salts, alkaline earth salts, e.g. Ca- and Mg-salts, and ammonium or alkyl-substituted ammonium salts, such as e.g. trimethylammonium salts. A preferred pharmaceutically acceptable salt of the compound of formula (I) is the sodium salt.

The term "η$^5$" means eta5 as used normally in coordination chemistry. It indicates the number of electrons shared between a metal center and a ligand in a coordination compound or complex.

The present invention relates to a process for the preparation of a compound of formula (I)

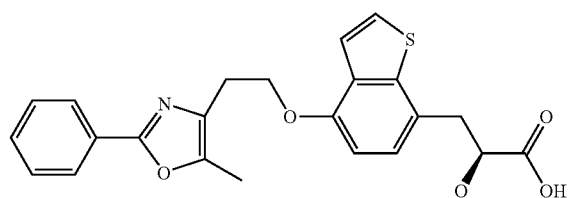

(I)

or a salt thereof, wherein a compound of formula (II)

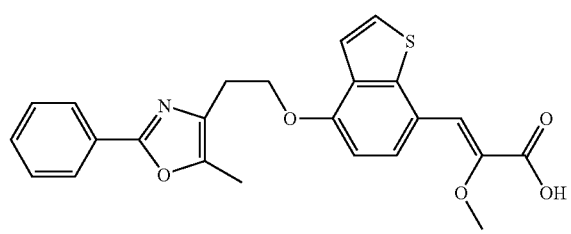

(II)

or a salt thereof is hydrogenated
(c) in the presence of a catalyst comprising iridium; or
(d) in the presence of a catalyst comprising ruthenium and a compound of: formula (IV),

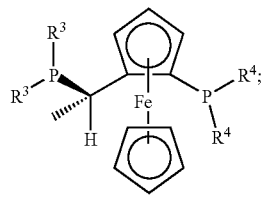

(IV)

formula (V),

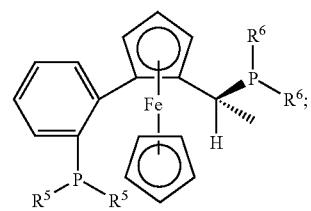

(V)

formula (VI),

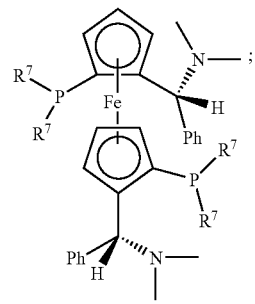

(VI)

or formula (VII),

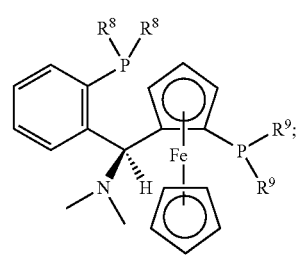

(VII)

wherein
$R^3$ is alkyl, cycloalkyl or aryl;
$R^4$ is cycloalkyl, aryl or heteroaryl;
$R^5$ is cycloalkyl or aryl;
$R^6$ is cycloalkyl or aryl;
$R^7$ is cycloalkyl or aryl;
$R^8$ is cycloalkyl or aryl; and
$R^9$ is cycloalkyl or aryl.

A preferred process is process according to the invention wherein the catalyst comprises iridium and a compound of formula (III),

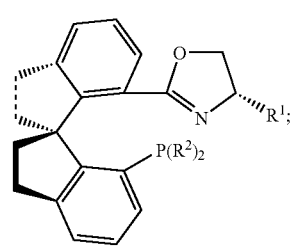

(III)

formula (VIII),

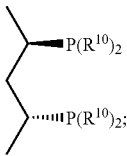

or formula (IX),

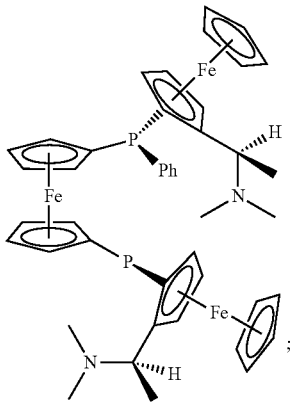

wherein
R$^1$ is hydrogen, alkyl, aryl or arylalkyl;
R$^2$ is aryl; and
R$^{10}$ is aryl.

Further preferred is a process according as defined above wherein the catalyst comprises iridium and a compound of formula (III)

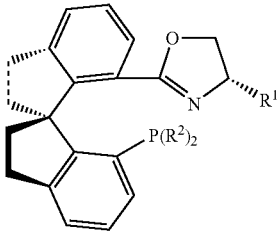

wherein R$^1$ and R$^2$ are as defined above.

Also particularly preferred is a process as defined above wherein the catalyst comprises iridium and a compound of formula (X)

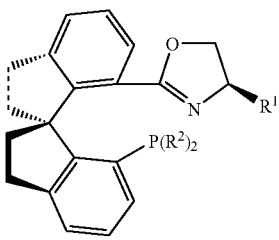

wherein R$^1$ and R$^2$ are as defined above.

R$^1$ is preferably hydrogen, alkyl, phenyl or benzyl, more preferably hydrogen, alkyl or benzyl.

In particular, a process as defined above wherein R$^1$ is hydrogen, iso-propyl, phenyl or benzyl is preferred. More preferably, R$^1$ is hydrogen, iso-propyl or benzyl.

Also preferred is a process as defined above wherein R$^2$ is phenyl or phenyl substituted with one or two alkyl.

Moreover, preferred is a process according to the invention wherein R$^2$ is phenyl, 3,5-di-methylphenyl or 3,5-di-tert-butyl-phenyl.

A process according to the invention wherein R$^{10}$ is 3,5-di-methyl-phenyl is further preferred.

The compound of formula (IX) is (S,R,R)-1,1'-bis-[((1-N,N-dimethylamino)ethylferrocenyl)(phenylphosphino)]ferrocene.

A preferred compound of formula (VIII) is (S,S)-[1,3-dimethyl-1,3-propanediyl]bis[di-(3,5-dimethylphenyl)phosphine].

Particularly preferred is a process according to the invention wherein the compound of formula (III) is
(S$_a$,S)-7-[4,5-Dihydro-4-benzyloxazol-2-yl]-7'-diphenylphosphino-1,1'-spirobiindane;
(S$_a$,S)-7-[4,5-Dihydro-4-benzyloxazol-2-yl]-7'-di(3,5-di-methylphenyl)phosphino-1,1'-spirobiindane;
(S$_a$,S)-7-[4,5-Dihydro-4-benzyloxazol-2-yl]-7'-di(3,5-di-tert-butylphenyl)phosphino-1,1'-spirobiindane;
(S$_a$,S)-7-[4,5-Dihydro-4-phenyloxazol-2-yl]-7'-di(3,5-di-tert-butylphenyl)phosphino-1,1'-spirobiindane;
(S$_a$,S)-7-[4,5-Dihydro-4-isopropyloxazol-2-yl]-7'-di(3,5-di-tert-butylphenyl)phosphino-1,1'-spirobiindane; or
(S$_a$)-7-[4,5-Dihydrooxazol-2-yl]-7'-di(3,5-di-tert-butylphenyl)phosphino-1,1'-spirobiindane.

Further preferred is a process according to the invention wherein the compound of formula (III) is
(S$_a$,S)-7-[4,5-Dihydro-4-benzyloxazol-2-yl]-7'-di(3,5-di-tert-butylphenyl)phosphino-1,1'-spirobiindane;
(S$_a$,S)-7-[4,5-Dihydro-4-isopropyloxazol-2-yl]-7'-di(3,5-di-tert-butylphenyl)phosphino-1,1'-spirobiindane; or
(S$_a$)-7-[4,5-Dihydrooxazol-2-yl]-7'-di(3,5-di-tert-butylphenyl)phosphino-1,1'-spirobiindane.

Still further preferred is a process according to the invention wherein the compound of formula (X) is (S$_a$,R)-7-[4,5-Dihydro-4-benzyloxazol-2-yl]-7'-diphenylphosphino-1,1'-spirobiindane;
(S$_a$,R)-7-[4,5-Dihydro-4-benzyloxazol-2-yl]-7'-di(3,5-di-methylphenyl)phosphino-1,1'-spirobiindane;
(S$_a$,R)-7-[4,5-Dihydro-4-benzyloxazol-2-yl]-7'-di(3,5-di-tert-butylphenyl)phosphino-1,1'-spirobiindane;
(S$_a$,R)-7-[4,5-Dihydro-4-phenyloxazol-2-yl]-7'-di(3,5-di-tert-butylphenyl)phosphino-1,1'-spirobiindane; or
(S$_a$,R)-7-[4,5-Dihydro-4-isopropyloxazol-2-yl]-7'-di(3,5-di-tert-butylphenyl)phosphino-1,1'-spirobiindane.

Moreover, preferred is a process as defined above wherein the catalyst is Ir(L$^1$)(L$^2$)$_n$Y wherein
Ir is iridium;
L$^1$ is a compound of formula (III), (VIII) or (IX) as defined above;
L$^2$ is cyclooctene, 1,5-cyclooctadiene, ethylene, 1,5-hexadiene or norbornadiene;
Y is chloride, iodide, bromide, fluoride, trifluoroacetate, tetrafluoroborate, tetrakis[3,5-bis(trifluoromethyl)phenyl]borate, tetraphenylborate, hexafluoroantimonate, hexafluorophosphate, triflate, mesylate, perchlorate, perbromate, periodate, nitrate, hydrogen sulfate or acetylacetonate; and
n is 1 or 2.

Also preferred is a process as defined above wherein the catalyst is Ir(L¹)(L²)$_n$Y wherein L¹ is a compound of formula (X) and wherein Ir, L², Y and n are as defined above.

Particularly preferred is a process wherein L¹ is a compound of formula (III).

Y is preferably chloride, tetrafluoroborate, hexafluorophosphate or tetrakis[3,5-bis(trifluoromethyl)phenyl]borate, more preferably tetrafluoroborate or tetrakis[3,5-bis(trifluoromethyl)phenyl]borate.

In particular, preferred is a process according to the invention wherein the catalyst is

[Ir((S,S)-7-[4,5-dihydro-4-benzyloxazol-2-yl]-7'-di(3,5-di-tert-butylphenyl)phosphino-1,1'-spirobiindane)(1,5-cyclooctadiene)][tetrakis[3,5-bis(trifluoromethyl)phenyl]borate];

[Ir((S,S)-7-[4,5-dihydro-4-benzyloxazol-2-yl]-7'-di(3,5-di-tert-butylphenyl)phosphino-1,1'-spirobiindane)(1,5-cyclooctadiene)][tetrafluoroborate];

[Ir((S,S)-7-[4,5-dihydro-4-benzyloxazol-2-yl]-7'-di(3,5-di-tert-butylphenyl)phosphino-1,1'-spirobiindane)(1,5-cyclooctadiene)][trifluoromethanesulfonate];

[Ir((S,S)-7-[4,5-dihydro-4-benzyloxazol-2-yl]-7'-di(3,5-di-tert-butylphenyl)phosphino-1,1'-spirobiindane)(1,5-cyclooctadiene)][chloride];

[Ir((S,S)-7-[4,5-dihydro-4-isopropyloxazol-2-yl]-7'-di(3,5-di-tert-butylphenyl)phosphino-1,1'-spirobiindane)(1,5-cyclooctadiene)][tetrakis[3,5-bis(trifluoromethyl)phenyl]borate]; or

[Ir((S)-7-[4,5-dihydrooxazol-2-yl]-7'-di(3,5-di-tert-butylphenyl)phosphino-1,1'-spirobiindane)(1,5-cyclooctadiene)][tetrakis[3,5-bis(trifluoromethyl)phenyl]borate].

Further particularly preferred is a process according to the invention wherein the catalyst is

[Ir((S$_a$,R)-7-[4,5-dihydro-4-benzyloxazol-2-yl]-7'-di(3,5-di-tert-butylphenyl)phosphino-1,1'-spirobiindane) (1,5-cyclooctadiene)][tetrakis[3,5-bis(trifluoromethyl)phenyl]borate];

[Ir((S$_a$,R)-7-[4,5-dihydro-4-benzyloxazol-2-yl]-7'-di(3,5-di-tert-butylphenyl)phosphino-1,1'-spirobiindane)(1,5-cyclooctadiene)][tetrafluoroborate];

[Ir((S$_a$,R)-7-[4,5-dihydro-4-benzyloxazol-2-yl]-7'-di(3,5-di-tert-butylphenyl)phosphino-1,1'-spirobiindane)(1,5-cyclooctadiene)][trifluoromethanesulfonate]; or

[Ir((S$_a$,R)-7-[4,5-dihydro-4-benzyloxazol-2-yl]-7'-di(3,5-di-tert-butylphenyl)phosphino-1,1'-spirobiindane)(1,5-cyclooctadiene)][chloride].

Also preferred is a process as defined above wherein the catalyst comprises ruthenium and a compound of formula (IV), (V), (VI) or (VII).

$R^3$ is preferably alkyl, cyclohexyl, phenyl, alkylphenyl or dialkylphenyl.

In particular, preferred is a process as defined above wherein $R^3$ is tert-butyl, cyclohexyl, phenyl, 2-methyl-phenyl or 3,5-di-methyl-phenyl.

Moreover, $R^4$ is preferably alkyl, cyclohexyl, phenyl, naphtyl, furyl or phenyl substituted with one to three substituents independently selected from trifluoromethyl, alkyl and alkoxy.

A process according to the invention wherein $R^4$ is tert-butyl, cyclohexyl, phenyl, 3,5-di-trifluoromethyl-phenyl, 4-trifluoromethyl-phenyl, 3,5-di-methyl-4-methoxy-phenyl, 1-naphtyl or 2-furyl is also preferred.

$R^5$ is preferably cyclohexyl, phenyl or phenyl substituted with one to three substituents independently selected from alkyl and alkoxy.

Furthermore, a process according to the invention wherein $R^5$ is phenyl, cyclohexyl, 3,5-di-methyl-4-methoxy-phenyl or 3,5-di-methyl-phenyl is also preferred.

$R^6$ is preferably cyclohexyl, norbornyl, phenyl or phenyl substituted with one to three substituents independently selected from alkyl and trifluoromethyl.

Moreover, preferred is a process as defined above wherein $R^6$ is phenyl, cyclohexyl, 3,5-di-methyl-phenyl, 3,5-di-trifluoromethyl-phenyl or norbornyl.

$R^7$ is preferably cyclohexyl, phenyl or phenyl substituted with one to three substituents independently selected from alkyl, trifluoromethyl and alkoxy.

Also preferred is a process according to the invention wherein $R^7$ is cyclohexyl, phenyl, 3,5-di-methyl-phenyl, 3,5-di-trifluoromethyl-phenyl, 3,5-di-methyl-4-methoxy-phenyl or 2-methyl-phenyl.

Particularly preferred is a process according to the invention wherein $R^8$ is cyclohexyl or phenyl.

A process according to the invention wherein $R^9$ is cyclohexyl or phenyl is further preferred.

Furthermore, particularly preferred is a process according to the invention wherein the compound of formula (IV), (V), (VI), (VII) or (VIII) is (S)-1-[(R)-2-(Diphenylphosphino)ferrocenyl]ethyldi-tert-butylphosphine;

(S)-1-[(R)-2-(Dicyclohexylphosphino)ferrocenyl]ethyldi-tert-butylphosphine;

(S)-1-[(R)-2-(Di-(4-trifluoromethylphenyl)phosphino)ferrocenyl]ethyldi-tert-butyl phosphine;

(S)-1-[(R)-2-(Di-(3,5-dimethyl-4-methoxyphenyl)phosphino)ferrocenyl]ethyldi-tert-butylphosphine;

(S)-1-[(R)-2-(Di-2-furylphosphino)ferrocenyl]ethyldi-tert-butylphosphine;

(αR,αR)-2,2'-Bis(α-N,N-dimethylaminophenylmethyl)-(S,S)-1,1'-bis(diphenylphosphino) ferrocene;

(αR,αR)-2,2'-Bis(α-N,N-dimethylaminophenylmethyl)-(S,S)-1,1'-bis[di(3,5-dimethyl-4-methoxyphenyl)phosphino] ferrocene;

(R)-1-Diphenylphosphino-2-[(S)-α-(N,N-dimethylamino)-o-diphenylphosphinophenyl)methyl]ferrocene;

(S)-1-[(S)-2-(2'-Diphenylphosphinophenyl)ferrocenyl]ethyldi(bis-3,5-trifluoromethyl phenyl)phosphine;

(R)-1-[(R)-2-(2'-Dicyclohexylphosphinophenyl)ferrocenyl]ethyldi(bis-3,5-trifluoromethylphenyl)phosphine; or (R)-1-[(R)-2-(2'-Diphenylphosphinophenyl)ferrocenyl]ethyldi-(2-norbornyl)phosphine.

Moreover, further preferred is a process according to the invention wherein the compound of formula (IV), (V), (VI) or (VII) is (S)-1-[(R)-2-(Diphenylphosphino)ferrocenyl]ethyldi-tert-butylphosphine; or (S)-1-[(R)-2-(Di-(3,5-dimethyl-4-methoxyphenyl)phosphino)ferrocenyl]ethyldi-tert-butylphosphine.

In particular, preferred is a process as defined above wherein the catalyst is Ru(L³)(L⁴)(L⁵)$_m$Y$_p$ wherein, Ru is ruthenium;

L³ is a compound of formula (IV), (V), (VI) or (VII) as defined above;

L⁴ is η⁵-2,4-dimethylpentadienyl, cyclopentadienyl or η⁵-2,3,4-trimethylpenta-dienyl;

L⁵ is halide, acetonitrile, diethyl ether, water, acetone, tetrahydrofuran, dioxane, pyridine, imidazole or thiophene;

Y is tetrakis[3,5-bis(trifluoromethyl)phenyl]borate, tetrafluoroborate, tetraphenylborate, hexafluoroantimonate, hexafluorophosphate, triflate, mesylate, hydrogen sulfate or perchlorate;

m is 0 or 1; and p is 0 or 1.

L⁵ is preferably iodine.

m is preferably 1. p is preferably 1.

Particularly preferred is a process as defined above wherein the catalyst is

[Ru(η⁵-2,4-dimethylpentadienyl)((S)-1-[(R)-2-(diphenylphosphino)ferrocenyl]ethyldi-tert-butylphosphine)(acetonitrile)][tetrafluoroborate];

[Ru(η⁵-2,4-dimethylpentadienyl)((S)-1-[(R)-2-(dicyclohexylphosphino)ferrocenyl]ethyldi-tert-butylphosphine)(acetonitrile)][tetrafluoroborate];

[Ru(η⁵-2,4-dimethylpentadienyl)((S)-1-[(R)-2-(di-(4-trifluoromethylphenyl)phosphino)ferrocenyl]ethyldi-tert-butylphosphine)(acetonitrile)][tetrafluoroborate];

[Ru(η⁵-2,4-dimethylpentadienyl)((S)-1-[(R)-2-(di-(3,5-dimethyl-4-methoxyphenyl)phosphino)ferrocenyl]ethyldi-tert-butylphosphine)(acetonitrile)][tetrafluoroborate];

[Ru(η⁵-2,4-dimethylpentadienyl)((S)-1-[(R)-2-(di-2-furylphosphino)ferrocenyl]ethyldi-tert-butylphosphine)(acetonitrile)][tetrafluoroborate];

[Ru(η⁵-2,4-dimethylpentadienyl)((αR,αR)-2,2'-bis(α-N,N-dimethylaminophenylmethyl)-(S,S)-1,1'-bis(diphenylphosphino)ferrocene) (acetonitrile)][tetrafluoroborate];

[Ru(η⁵-2,4-dimethylpentadienyl)((αR,αR)-2,2'-bis(α-N,N-dimethylaminophenylmethyl)-(S,S)-1,1'-bis[di(3,5-dimethyl-4-methoxyphenyl)phosphino]ferrocene)(acetonitrile)][tetrafluoroborate];

[RuI(η⁵-2,4-dimethylpentadienyl)((R)-1-diphenylphosphino-2-[(S)-α-(N,N-dimethylamino)-o-diphenylphosphinophenyl)methyl]ferrocene)];

[Ru(η⁵-2,4-dimethylpentadienyl)((S)-1-[(S)-2-(2'-diphenylphosphinophenyl)ferrocenyl]ethyldi(bis-3,5-trifluoromethylphenyl)phosphine)(acetonitrile)][tetrafluoroborate];

[Ru(η⁵-2,4-dimethylpentadienyl)((R)-1-[(R)-2-(2'-dicyclohexylphosphinophenyl)ferrocenyl]ethyldi(bis-3,5-trifluoromethylphenyl)phosphine)(acetonitrile)][tetrafluoroborate]; or

[Ru(η⁵-2,4-dimethylpentadienyl)((R)-1-[(R)-2-(2'-diphenylphosphinophenyl)ferrocenyl]ethyldi-(2-norbornyl)phosphine)(acetonitrile)][tetrafluoroborate].

Further particularly preferred is a process according to the invention wherein the catalyst is

[Ru(5-2,4-dimethylpentadienyl)((S)-1-[(R)-2-(diphenylphosphino)ferrocenyl]ethyldi-tert-butylphosphine)(acetonitrile)][tetrafluoroborate]; or

[Ru(η⁵-2,4-dimethylpentadienyl)((S)-1-[(R)-2-(di-(3,5-dimethyl-4-methoxyphenyl)phosphino)ferrocenyl]ethyldi-tert-butylphosphine)(acetonitrile)][tetrafluoroborate].

According to the invention, the compound of formula (II) can be hydrogenated under a pressure of hydrogen gas.

When an iridium catalyst is used, the process is preferably carried out at a temperature of 10 to 120° C., more preferably 40 to 100° C., particularly preferably 60 to 80° C.

When a catalyst comprising iridium is used, the process is preferably carried out in a solvent selected from alcohols, fluorinated alcohols, tetrahydrofuran, methyl-tetrahydrofuran, dichloromethane, dialkyl ethers, aromatic solvents such as benzene, toluene, $CF_3$—$C_6H_5$, mono- and poly-fluorinated aromatic solvents and mixtures thereof, more preferred in methanol, tetrahydrofuran, dichloromethane and mixtures thereof, most preferably in methanol/tetrahydrofuran 3:2.

When a catalyst comprising iridium is used, the process is preferably carried out under a hydrogen pressure range of 1 to 200 bar, more preferably 10 to 100 bar, particularly preferably 40 to 60 bar. When the ligand of formula (III) of (S,S) configuration is used, preferred is a pressure of 10 bar. When the ligand of formula (III) of $(S_a,R)$ configuration is used, preferred is a pressure of 30 bar.

When a catalyst comprising iridium is used, the substrate-to-catalyst ratio (mol/mol) is preferably 10 to 50000, more preferably between 100 and 10000, particularly preferably between 1000 and 5000.

When a catalyst comprising ruthenium is used, the process is preferably carried out at a temperature of 10 to 120° C., more preferably 20 to 80° C., particularly preferably 30 to 50° C.

When a catalyst comprising ruthenium is used, the process is preferably carried out in a solvent selected from alcohols, tetrahydrofuran, dichloromethane, fluorinated alcohols, methyl-tetrahydrofuran, ethers and mixtures thereof, preferably methanol, tetrahydrofuran, dichloromethane and mixtures thereof, more preferably in a mixture dichloromethane/tetrahydrofuran 1:1 or in dichloromethane and particularly preferably in dichloromethane.

When a catalyst comprising ruthenium is used, the process is preferably carried out under a hydrogen pressure of 1 to 200 bar, more preferably 10 to 100 bar, particularly preferably 40 to 60 bar.

When a catalyst comprising ruthenium is used, the substrate-to-catalyst ratio (mol/mol) is preferably 10 to 50000, more preferably 100 to 10000, particularly preferably 1000 to 5000.

The preferred (S) configuration of the compound of formula (I) has been obtained with the ligands disclosed in the tables in the experimental part. Should a chiral ligand or catalyst afford preferentially the compound of formula (I) with the (R) configuration, it is clear that the ligand or catalyst with the opposite configuration should be used in order to obtain the compound of formula (I) with the (S) configuration. Both enantiomers of the chiral ligands are equally well accessible.

The invention also relates to a compound of formula (I) as defined above or a salt thereof obtained by a process according to the invention.

Furthermore, the invention also relates to the use of a catalyst as defined above for the preparation of a compound of formula (I) as defined above.

The catalysts for use in the process of the present invention may be prepared by reacting a compound of formula [Ir(L)Cl]₂, [Ir(L)₂]BARF or [Ir(L)₂]BF₄ where L denotes a neutral ligand, e.g. COD with the desired ligand of formula (III), (VIII), (IX) or (X), e.g. (S,S)-3,5-Xyl-Skewphos or (S,R,R)-TRIFER, in an appropriate solvent, such as e.g. dichloromethane or methanol. The catalyst may be used after isolation or as prepared in situ. The compounds [Ir(COD)Cl]₂ and [Ir⁺(COD)₂]BF₄ are either commercially available, e.g. from Strem Chemicals Inc., Newburgport, Mass. USA or can be prepared according to methods known per se, e.g. J. Herde et al., Inorg. Syn. 1974, 18-20 or M. Green et al., J. Chem. Soc. 1971, 2334-2337.

The term "neutral ligand" as used herein denotes a readily exchangeable ligand such as an olefin, e.g. ethylene, propylene, cyclooctene, 1,5-hexadiene, norbornadiene, 1,5-cyclooctadiene, a nitrile such as acetonitrile or benzonitrile, or also a solvent such as e.g. tetrahydrofuran, toluene etc. Where more than one such ligand is present, these can also be different from each other. A preferred neutral ligand is cyclooctadiene.

EXAMPLES

Abbreviations $\eta^5$-2,4-DMP=$\eta^5$-2,4-dimethylpentadienyl,

THF=tetrahydrofuran,

NCMe=acetonitrile,

TFA=trifluoroacetic acid,

COD=1,5-cyclooctadiene,

BARF=tetrakis[3,5-bis(trifluoromethyl)phenyl]borate, r.t.=room temperature,

S/C=substrate-to-catalyst ratio (mol/mol),

HPLC=high pressure liquid chromatography, ee=enantiomeric excess=[(S)−(R)]/[(S)+(R)].

DBT=DTB=3,5-di-tert.-butylphenyl

Triflate=trifluoromethanesulfonate

All ferrocenyl-diphosphine ligands are commercially available from Solvias AG, CH-4002 Basel. The ruthenium complexes are commercially available from Umicore AG, D-63457 Hanau-Wolfgang or can be prepared according to O. Briel et al. in "Catalysis of Organic Reactions", 2009, 203, CRC Press, Boca Raton. The oxazoline-monophosphine ligands (SIPHOX ligands) and their corresponding iridium complexes are commercially available from Nankai University, Tianjin 300071 China or can be prepared according to Q. L. Zhou et al. J. Am. Chem. Soc. 2008, 130, 8584. Xyl-Skewphos and 3,5-tBu-MeOBIPHEP are commercially available from Solvias AG, CH-4002 Basel. TRIFER is commercially available from Phoenix Chemicals, 34 Thursby Rod., Bromborough, Wirral CH62, 3PW, United Kingdom (UK) or can be prepared according to P. McCormack et al. Angew. Chem. Int. Ed. 2007, 46, 4141-44.

The atom numbering of SIPHOX ligands is shown below:

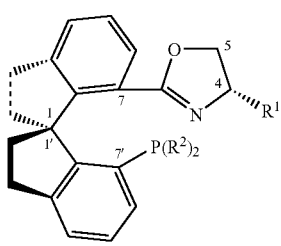

The asymmetric configuration of the ($S_a$,R) SIPHOX ligand is shown below:

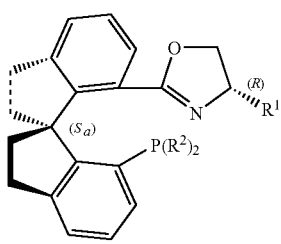

The ($S_a$,S) configuration of the SIPHOX ligand may also be noted (S,S).

| Chiral phosphorus Ligands | |
|---|---|
| Acronyms | Chemical Name |
| Ph-Bn-SIPHOX | 7-[4,5-Dihydro-4-benzyloxazol-2-yl]-7'-diphenylphosphino-1,1'-spirobiindane |
| Xyl-Bn-SIPHOX | 7-[4,5-Dihydro-4-benzyloxazol-2-yl]-7'-di(3,5-di-methylphenyl)phosphino-1,1'-spirobiindane |
| DBT-Bn-SIPHOX | 7-[4,5-Dihydro-4-benzyloxazol-2-yl]-7'-di(3,5-di-tert-butylphenyl) phosphino-1,1'-spirobiindane |
| DBT-Ph-SIPHOX | 7-[4,5-Dihydro-4-phenyloxazol-2-yl]-7'-di(3,5-di-tert-butylphenyl) phosphino-1,1'-spirobiindane |
| DBT-iPr-SIPHOX | 7-[4,5-Dihydro-4-isopropyloxazol-2-yl]-7'-di(3,5-di-tert-butylphenyl) phosphino-1,1'-spirobiindane |
| DBT-H-SIPHOX | 7-[4,5-Dihydrooxazol-2-yl]-7'-di(3,5-di-tert-butylphenyl)phosphino-1,1'-spirobiindane |
| TRIFER | 1,1'-Bis-[((1-N,N-dimethylamino)ethylferrocenyl)-(phenylphosphino)]ferrocene |
| Xyl-Skewphos | [1,3-Dimethyl-1,3-propanediyl]bis[di-(3,5-dimethylphenyl)phosphine] |
| PPF-PtBu$_2$ | 1-[2-(Diphenylphosphino)ferrocenyl]ethyldi-tert.-butylphosphine |
| Cy$_2$PF-PtBu$_2$ | 1-[2-(Dicyclohexylphosphino)-ferrocenyl]ethyldi-tert.-butylphosphine |
| (4-CF$_3$Ph)$_2$PF-PtBu$_2$ | 1-[2-(Di-(4-trifluoromethylphenyl)-phosphino)ferrocenyl]ethyldi-tert.-butylphosphine |
| (3,5-Me$_2$-4-MeOPh)$_2$PF-PtBu$_2$ | 1-[2-(Di-(3,5-dimethyl-4-methoxyphenyl)-phosphino)ferrocenyl]ethyldi-tert.-butylphosphine |
| 2-Fur$_2$PF-PtBu$_2$ | 1-[2-(Di-2-furylphosphino)ferrocenyl]ethyldi-tert.-butylphosphine |
| NMe$_2$-PPh$_2$-Mandyphos | 2,2'-Bis(α-N,N-dimethylaminophe-nylmethyl)-1,1'-bis(diphenylphosphino) ferrocene |
| NMe$_2$-P(3,5-Me-4-MeOPh)$_2$-Mandyphos | 2,2'-Bis(α-N,N-dimethylaminophenylmethyl)-1,1'-bis[di(3,5-dimethyl-4-methoxyphenyl)-phosphino]ferrocene |
| PPPhCHNMe$_2$-F-PP | 1-Diphenylphosphino-2-[α-(N,N-dimethylamino)-o-diphenylphosphinophenyl)-methyl]ferrocene |
| PPPhFCHCH$_3$-P(3,5-CF$_3$Ph)$_2$ | 1-[2-(2'-Diphenylphosphinophenyl)ferrocenyl]-ethyldi(bis-3,5-trifluoromethylphenyl)-phosphine |
| Cy$_2$PPhFCH CH$_3$P(3,5-CF$_3$Ph)$_2$ | 1-[2-(2'-Dicyclohexylphosphino phenyl)ferrocenyl]ethyldi(bis-3,5-trifluoromethylphenyl)phosphine |
| PPPhFCHCH$_3$-P(Norbornyl)$_2$ | 1-[2-(2'-Diphenylphosphinophenyl)-ferrocenyl]ethyldi-(2-norbornyl)phosphine |

Synthesis of Iridium Metal Complexes

Examples 1a-1h

Example 1.a

Preparation of [Ir((S,S)-Xyl-Skewphos)(COD)]BF$_4$

A 25-ml Schlenk tube was charged with 100 mg of (S,S)-Xyl-Skewphos (0.18 mmol), 60 mg of [Ir(COD)Cl]$_2$ (0.09 mmol) and 5 ml of dichloromethane. To the formed dark red solution, 35 mg of silver tetrafluoroborate (0.18 mmol) was added in two portions and the resulting suspension was stirred for 2 hours at r.t. The reaction mixture was filtered over dicalite speedex and the filter cake was washed with 6 ml of dichloromethane. The combined filtrates were rotary evaporated to dryness (50° C./5 mbar). The formed crude product was washed with 8 ml of hexane and dried over high vacuum to afford 563 mg (85%) of [Ir((S,S)-Xyl-Skewphos)(COD)]BF$_4$ as a red solid. FT-MS: 853.4 m/z [Ir((S,S)-Xyl-Skewphos)(COD)]$^+$, $^{31}$P-NMR (CDCl$_3$): 14.6 ppm (s).

Example 1.b

Preparation of [Ir((S,R,R)-Trifer)(COD)]BARF

A 100-ml Schlenk tube was charged with 400 mg of (S,R,R)-TRIFER (0.44 mmol), 584 mg of Ir(COD)$_2$]BARF (0.46 mmol) and 40 ml of methanol. The formed orange solution was stirred for 5 hours at r.t. Then, 12 ml of water was added and the formed crystals were filtered off. The filter cake was washed with 32 ml of a mixture of methanol/water (4:1) and dried over high vacuum to afford 804 mg (88%) of [Ir((S,R,R)-TRIFER)(COD)]BARF as orange crystals. FT-MS: 1213.2 m/z [Ir((S,R,R)-TRIFER)(COD)]$^+$. $^{31}$P-NMR (CDCl$_3$): 6.2 ppm (s).

Example 1.c

Preparation of [Ir((S$_a$,R)-DBT-Bn-SIPHOX)(COD)]BARF

A 25-ml Schlenk tube was charged with 100 mg of (S$_a$,R)-DBT-Bn-SIPHOX (0.127 mmol), 168 mg of [Ir(COD)$_2$]BARF (0.132 mmol) and 10 ml of methanol. To the formed yellow solution was stirred for 2 hours at r.t., then the reaction mixture rotary evaporated to dryness (50° C./5 mbar). The residue was dissolved in 5 ml of methanol. 0.5 ml of water was added and the formed yellow suspension was stirred for 30 min at r.t. The crystals were filtered off, washed with 3.5 ml of MeOH/water (6:1) and dried over high vacuum to afford 189 mg (76%) of [Ir((S$_a$,R)-DBT-Bn-SIPHOX)(COD)]BARF as an orange solid. FT-MS: 1088.5 m/z [Ir((S$_a$,R)-DBT-Bn-SIPHOX)(COD)]$^+$, $^{31}$P-NMR (CDCl$_3$): 16.5 ppm (s).

Example 1.d

Preparation of [Ir((S$_a$,R)-DBT-Bn-SIPHOX)(COD)]BF$_4$

A 25-ml Schlenk tube was charged with 56 mg of (S$_a$,R)-DBT-Bn-SIPHOX (0.070 mmol), 24 mg of [Ir(COD)Cl]$_2$ (0.035 mmol) and 5 ml of dichloromethane. To the formed orange solution, 14 mg of silver tetrafluoroborate (0.071 mmol) was added and the resulting orange suspension was stirred for 2 hours at r.t. The reaction mixture was filtered over dicalite speedex and the filter cake was washed with 9 ml of dichloromethane. The combined filtrates were rotary evaporated to dryness (50° C./5 mbar). The formed crude product was washed with 11 ml of hexane and dried over high vacuum to afford 69 mg (83%) of [Ir((S$_a$,R)-DBT-Bn-SIPHOX)(COD)]BF$_4$ as an orange solid. FT-MS: 1088.5 m/z [Ir((S$_a$,R)-DBT-Bn-SIPHOX)(COD)]$^+$, $^{31}$P-NMR (CDCl$_3$): 16.6 ppm (s).

Example 1.e

Preparation of [Ir((R$_a$,S)-DBT-Bn-SIPHOX)(COD)]OTf

A 25-ml Schlenk tube was charged with 100 mg of (R$_a$,S)-DBT-Bn-SIPHOX (0.127 mmol), 44 mg of [Ir(COD)Cl]$_2$ (0.505 mmol) and 4 ml of dichloromethane. To the formed orange solution, 34 mg of silver trifluoromethanesulfonate (0.130 mmol) was added and the resulting orange suspension was stirred for 2 hours at r.t. The reaction mixture was filtered over dicalite speedex and the filter cake was washed with 6 ml of dichloromethane. The combined filtrates were rotary evaporated to dryness (50° C./5 mbar). The formed crude product was washed with 11 ml of hexane and dried over high vacuum to afford 134 mg (85%) of [Ir((R$_a$,S)-DBT-Bn-SIPHOX)(COD)]OTf as an orange solid. FT-MS: 1088.5 m/z [Ir((R$_a$,S)-DBT-Bn-SIPHOX)(COD)]$^+$, $^{31}$P-NMR (CDCl$_3$): 16.6 ppm (s).

Example 1.f

Preparation of [Ir((S,S)-DBT-Bn-SIPHOX)(COD)]BF$_4$

A 25-ml Schlenk tube was charged with 100 mg of (S,S)-DBT-Bn-SIPHOX (0.127 mmol), 43 mg of [Ir(COD)Cl]$_2$ (0.063 mmol) and 5 ml of dichloromethane. To the formed orange solution, 26 mg of silver tetrafluoroborate (0.131 mmol) was added and the resulting orange suspension was stirred for 2 hours at r.t. The reaction mixture was filtered over dicalite speedex and the filter cake was washed with 6 ml of dichloromethane. The combined filtrates were rotary evaporated to dryness (50° C./5 mbar). The formed crude product was washed with 8 ml of hexane and dried over high vacuum to afford 148 mg (99%) of [Ir((S,S)-DBT-Bn-SIPHOX)(COD)]BF$_4$ as an orange solid. FT-MS: 1088.5 m/z [Ir((S,S)-DBT-Bn-SIPHOX)(COD)]$^+$, $^{31}$P-NMR (CDCl$_3$): 16.0 ppm (s).

Example 1.g

Preparation of [Ir((S,S)-DBT-Bn-SIPHOX)(COD)]BF$_4$

A 25-ml Schlenk tube was charged with 200 mg of (S,S)-DBT-Bn-SIPHOX (0.254 mmol), 87 mg of [Ir(COD)Cl]$_2$ (0.128 mmol) and 5 ml of dichloromethane. To the formed orange solution, 43 mg of sodium tetrafluoroborate (0.384 mmol) was added and the resulting orange suspension was stirred for 5 hours at r.t. The reaction mixture was filtered over dicalite speedex and the filter cake was washed with 8 ml of dichloromethane. The combined filtrates were rotary evaporated to dryness (50° C./5 mbar). The formed crude product was washed with 11 ml of hexane and dried over high vacuum to afford 259 mg (87%) of [Ir((S,S)-DBT-Bn-SIPHOX)(COD)]BF$_4$ as an orange solid. FT-MS: 1088.5 m/z [Ir((S,S)-DBT-Bn-SIPHOX)(COD)]$^+$, $^{31}$P-NMR (CDCl$_3$): 16.0 ppm (s).

Example 1.h

Preparation of [Ir((R$_a$,S)-DBT-Bn-SIPHOX)(COD)]BF$_4$

A 25-ml Schlenk tube was charged with 40 mg of (R$_a$,S)-DBT-Bn-SIPHOX (0.058 mmol), 18 mg of [Ir(COD)Cl]$_2$ (0.026 mmol) and 4 ml of dichloromethane. To the formed orange solution, 9 mg of sodium tetrafluoroborate (0.076 mmol) was added and the resulting orange suspension was stirred for 3 hours at r.t. The reaction mixture was filtered over dicalite speedex and the filter cake was washed with 6 ml of dichloromethane. The combined filtrates were rotary evaporated to dryness (50° C./5 mbar). The formed crude product was washed with 11 ml of hexane and dried over high vacuum to afford 51 mg (86%) of [Ir((R$_a$,S)-DBT-Bn-SIPHOX)

(COD)]BF$_4$ as an orange solid. FT-MS: 1088.5 m/z [Ir((R$_a$, S)-DBT-Bn-SIPHOX)(COD)]$^+$, $^{31}$P-NMR (CDCl$_3$): 16.6 ppm (s).

Synthesis of 2-Methoxy-3-{4-[2-(5-methyl-2-phenyl-oxazol-4-yl)-ethoxy]-benzo[b]thiophen-7-yl}-propionic acid via asymmetric hydrogenation of (Z)-2-methoxy-3-{4-[2-(5-methyl-2-phenyl-oxazol-4-yl)-ethoxy]-benzo[b]thiophen-7-yl}-acrylic acid Examples 2-19 & Comparative Example A Example 2.1

In a glove box (O$_2$ content≦2 ppm), a 185-ml stainless steel autoclave was charged with 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 35.9 mg of [Ir((S,S)-DBT-Bn-SIPHOX)(COD)]BARF (0.018 mmol, S/C 250), 24 ml of methanol, 16 ml of tetrahydrofuran and 0.12 ml of (S)-1-phenylethylamine (0.93 mmol). The autoclave was sealed and the hydrogenation was run at 60° C. under 30 bar of hydrogen. After 16 h the autoclave was opened and the yellowish solution was rotary evaporated to dryness (50° C./5 mbar) to afford crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 99.6% (>99.9% conversion) and an enantiomeric purity of 99.5%.

HPLC method for chemical purity (area-%, (S)-phenylethylamine not included): YMC-Pack Pro C18, 150×4.6 mm; mobile phase A: mobile phase A: water with 0.1% TFA, B: NCMe with 0.1% TFA, 22° C., 2 ml/min, isocratic A/B 51/49% during 10 min, gradient from 51/49% to 5/95% within 10 min and 5 min at 5/95%, 285 nm. Retention times: 11.2 min (S)- and (R)-2-methoxy-3-{4-[2-(5-methyl-2-phenyl-oxazol-4-yl)-ethoxy]-benzo[b]thiophen-7-yl}-propionic acid; 12.4 min (E)-2-methoxy-3-{4-[2-(5-methyl-2-phenyl-oxazol-4-yl)-ethoxy]-benzo[b]thiophen-7-yl}-acrylic acid; 14.0 min (Z)-2-methoxy-3-{4-[2-(5-methyl-2-phenyl-oxazol-4-yl)-ethoxy]-benzo[b]thiophen-7-yl}-acrylic acid.

HPLC method for ee determination (area-%): Chiralpak-ADH column, 25 cm×4.6 mm, 85% heptane/10% ethanol with 0.4% trifluoroacetic acid, flow 0.7 ml/min, 30° C., 270 nm. Retention times: 22.4 min (R)-2-methoxy-3-{4-[2-(5-methyl-2-phenyl-oxazol-4-yl)-ethoxy]-benzo[b]thiophen-7-yl}-propionic acid; 26.3 min (S)-2-methoxy-3-{4-[2-(5-methyl-2-phenyl-oxazol-4-yl)-ethoxy]-benzo[b]thiophen-7-yl}-propionic acid.

Example 2.2

In a glove box (O$_2$ content≦2 ppm), a 185-ml stainless steel autoclave was charged with 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 2.70 mg of [Ir((S$_a$,R)-DBT-Bn-SIPHOX)(COD)]BF$_4$ (0.0023 mmol, S/C 2,000), 24 ml of methanol, 16 ml of tetrahydrofuran and 0.12 ml of (S)-1-phenylethylamine (0.92 mmol). The autoclave was sealed and the hydrogenation was run under 30 bar of hydrogen at 60° C. for 20 h and subsequently at 80° C. for 2 h. Then the autoclave was opened and the yellowish solution was rotary evaporated to dryness (50° C./5 mbar) to afford crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 89.9% (>99.9% conversion) and an enantiomeric purity of 99.8%. The crude product was dissolved in 50 ml of ethyl acetate. 10 ml of water and 3 ml of 2M aqueous HCl were added and the biphasic mixture was stirred at 55° C. for 15 min. The organic layer was separated, the aqueous layer extracted with 20 ml of ethyl acetate and the combined organic layers stirred over 0.5 g of carcoal (Darko KB) at r.t. for 2 h. After filtration over celite, the colorless solution was dried over 3 g of sodium sulfate and evaporated to dryness (40° C./10 mbar). The crude product was dissolved in 50 ml of isopropyl acetate at reflux (oil bath temp. 100° C.) and allowed to cool to room temperature whereby crystallization started spontaneously. The formed crystals were filtered off, washed with 10 ml of isopropyl acetate and dried at 75° C./500 mbar for 4 h to yield 1.60 g (79%) of pure (S)-2-methoxy-3-{4-[2-(5-methyl-2-phenyl-oxazol-4-yl)-ethoxy]-benzo[b]thiophen-7-yl}-propionic acid (Acid I) as a white crystals with a chemical purity of 99.6% and an enantiomeric purity of 99.8% ee.

Examples 3.1-3.4

In an analogous manner to Example 2 the following hydrogenations were performed at 60° C. under 30 bar of hydrogen (reaction time: 16 h) using iridium complexes of general formula [Ir(Phosphorous Ligand)(COD)]BARF as catalysts to afford crude 2-methoxy-3-{4-[2-(5-methyl-2-phenyl-oxazol-4-yl)-ethoxy]-benzo[b]thiophen-7-yl}-propionic acid (Acid I) as listed in Table 1.

TABLE 1

| Exp. No. | Phosphorus Ligand | Conv. [%] | Acid I Purity [%] | Acid I Ee [%]/ Configuration |
|---|---|---|---|---|
| 3.1 | (S,S)-Xyl-Bn-SIPHOX | 99.8 | 97.6 | 88.9/S |
| 3.2 | (S,S)-DBT-Ph-SIPHOX | 99.9 | 99.4 | 98.0/S |
| 3.3 | (S,S)-DBT-iPr-SIPHOX | >99.9 | 99.3 | 99.3/S |
| 3.4 | (S)-DBT-H-SIPHOX | >99.9 | 98.3 | 99.3/S |

Example 4

In a glove box (O$_2$ content≦2 ppm), a 185-ml stainless steel autoclave was charged with 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 8.96 mg of [Ir((S,S)-DBT-Bn-SIPHOX)(COD)]BARF (0.0046 mmol, S/C 1,000), 24 ml of methanol, 16 ml of tetrahydrofuran and 0.12 ml of (S)-1-phenylethylamine (0.93 mmol). The autoclave was sealed and the hydrogenation was run at 60° C. under 30 bar of hydrogen. After 16 h the autoclave was opened and the yellowish solution was rotary evaporated to dryness (50° C./5 mbar) to afford the crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 99.2% (99.8% conversion) and an enantiomeric purity of 99.3%.

Examples 5.1-5.2

In an analogous manner to Example 4 the following hydrogenations were performed at 60° C. under 30 bar of hydrogen (reaction time: 16 h) using iridium complexes of general formula [Ir(Phosphorus Ligand)(COD)]BARF as catalysts to afford crude 2-methoxy-3-{4-[2-(5-methyl-2-phenyl-oxazol-4-yl)-ethoxy]-benzo[b]thiophen-7-yl}-propionic acid (Acid I) as listed in Table 2.

TABLE 2

| Exp. No. | Phosphorus Ligand | Conv. [%] | Acid I Purity [%] | Acid I Ee [%]/ Configuration |
|---|---|---|---|---|
| 5.1 | (S,S)-DBT-iPr-SIPHOX | 99.9 | 99.5 | 98.7/S |
| 5.2 | (S)-DBT-H-SIPHOX | 99.9 | 98.1 | 99.3/S |

Example 6.1

In a glove box ($O_2$ content≦2 ppm), a 185-ml stainless steel autoclave was charged with 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 4.48 mg of [Ir((S,S)-DBT-Bn-SIPHOX)(COD)]BARF (0.0023 mmol, S/C 2,000), 24 ml of methanol, 16 ml of tetrahydrofuran and 0.12 ml of (S)-1-phenylethylamine (0.93 mmol). The autoclave was sealed and the hydrogenation was run at 60° C. for 20 h and subsequently 80° C. for 2 h under 30 bar of hydrogen. After the autoclave was opened and the yellowish solution was rotary evaporated to dryness (50° C./5 mbar) to afford crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 99.2% (>99.9% conversion) and an enantiomeric purity of 99.4%.

Example 6.2

In a glove box ($O_2$ content≦2 ppm), a 185-ml stainless steel autoclave was charged with 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 4.48 mg of [Ir(($S_a$,R)-DBT-Bn-SIPHOX)(COD)]BARF (0.0023 mmol, S/C 2,000), 24 ml of methanol, 16 ml of tetrahydrofuran and 0.12 ml of (S)-1-phenylethylamine (0.92 mmol). The autoclave was sealed and the hydrogenation was run under 30 bar of hydrogen at 60° C. for 20 h and subsequently at 80° C. for 2 h. Then the autoclave was opened and the yellowish solution was rotary evaporated to dryness (50° C./5 mbar) to afford crude (5)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 99.0% (>99.9% conversion) and an enantiomeric purity of 99.8%.

Example 7

In a glove box ($O_2$ content≦2 ppm), a 185-ml stainless steel autoclave was charged with 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 8.96 mg of [Ir((S,S)-DBT-Bn-SIPHOX)(COD)]BARF (0.0046 mmol, S/C 1,000), 24 ml of methanol, 16 ml of tetrahydrofuran and 0.12 ml of (S)-1-phenylethylamine (0.93 mmol). The autoclave was sealed and the hydrogenation was run at 60° C. for 8 h and subsequently 80° C. for 2 h under 30 bar of hydrogen. After the autoclave was opened and the yellowish solution was rotary evaporated to dryness (50° C./5 mbar) to afford 2.24 g of the crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 99.2% (>99.9% conversion) and an enantiomeric purity of 99.2%. The crude product was dissolved in 50 ml of ethyl acetate. 10 ml of water and 3 ml of 2M aqueous HCl were added and the biphasic mixture was stirred at 55° C. for 15 min. The organic layer was separated, the aqueous layer extracted with 20 ml of ethyl acetate and the combined organic layers stirred over 0.5 g of carcoal (Darko KB) at r.t. for 30 min. After filtration over celite, the colorless solution was dried over 3 g of sodium sulfate and evaporated to dryness (40° C./10 mbar). The crude product was dissolved in 50 ml of isopropyl acetate at reflux (oil bath temp. 100° C.) and allowed to cool to room temperature whereby crystallization started spontaneously. The formed crystals were filtered off, washed with 10 ml of isopropyl acetate and dried at 60° C./10 mbar for 2 h to yield 1.40 g (70%) of pure (S)-2-methoxy-3-{4-[2-(5-methyl-2-phenyl-oxazol-4-yl)-ethoxy]-benzo[b]thiophen-7-yl}-propionic acid (Acid I) as a white crystals with a chemical purity of 99.8% and an enantiomeric purity of >99.9% ee.

Example 8.1

In a glove box ($O_2$ content≦2 ppm), a 185-ml stainless steel autoclave was charged with 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 4.48 mg of [Ir((S,S)-DBT-Bn-SIPHOX)(COD)]BARF (0.0023 mmol, S/C 2,000), 24 ml of methanol, 16 ml of tetrahydrofuran and 0.12 ml of (S)-1-phenylethylamine (0.93 mmol). The autoclave was sealed and the hydrogenation was run at 60° C. for 20 h and subsequently 80° C. for 2 h under 10 bar of hydrogen. After the autoclave was opened and the yellowish solution was rotary evaporated to dryness (50° C./5 mbar) to afford crude (S)-2-methoxy-3-{4-[2-(5-methyl-2-phenyl-oxazol-4-yl)-ethoxy]-benzo[b]thiophen-7-yl}-prop ionic acid (Acid I) as a white solid with a chemical purity of 98.9% (>99.9% conversion) and an enantiomeric purity of 99.6%.

Example 8.2

In a glove box ($O_2$ content≦2 ppm), a 185-ml stainless steel autoclave was charged with 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 5.40 mg of [Ir(($S_a$,R)-DBT-Bn-SIPHOX)(COD)]$BF_4$ (0.0046 mmol, S/C 1,000), 24 ml of methanol, 16 ml of tetrahydrofuran and 0.12 ml of (S)-1-phenylethylamine (0.92 mmol). The autoclave was sealed and the hydrogenation was run at 60° C. for 20 h and subsequently 80° C. for 2 h under 10 bar of hydrogen. After the autoclave was opened and the yellowish solution was rotary evaporated to dryness (50° C./5 mbar) to afford crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 89.7% (91.1% conversion) and an enantiomeric purity of 99.8%.

Example 8.3

In a glove box ($O_2$ content≦2 ppm), a 185-ml stainless steel autoclave was charged with 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 2.84 mg of [Ir(($R_a$,S)-DBT-Bn-SIPHOX)(COD)]OTf (0.0023 mmol, S/C 2,000), 24 ml of methanol, 16 ml of tetrahydrofuran and 0.12 ml of (S)-1-phenylethylamine (0.92 mmol). The autoclave was sealed and the hydrogenation was run at 60° C. for 20 h and subsequently 80° C. for 2 h under 30 bar of hydrogen. After the autoclave was opened and the yellowish solution was rotary evaporated to dryness (50° C./5 mbar) to afford crude (R)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 98.7% (99.7% conversion) and an enantiomeric purity of 99.8%.

Example 8.4

In a glove box (O$_2$ content≦2 ppm), a 185-ml stainless steel autoclave was charged with 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 1.80 mg of [Ir((S$_a$,R)-DBT-Bn-SIPHOX)(COD)]BF$_4$ (0.0015 mmol, S/C 3,000), 24 ml of methanol, 16 ml of tetrahydrofuran and 0.12 ml of (S)-1-phenylethylamine (0.92 mmol). The autoclave was sealed and the hydrogenation was run at 60° C. for 20 h and subsequently 80° C. for 2 h under 60 bar of hydrogen. After the autoclave was opened and the yellowish solution was rotary evaporated to dryness (50° C./5 mbar) to afford crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 98.3% (99.4% conversion) and an enantiomeric purity of 99.7%.

Example 8.5

In a glove box (O$_2$ content≦2 ppm), a 185-ml stainless steel autoclave was charged with 0.77 mg of [Ir(COD)Cl]$_2$ (0.0012 mmol, S/C 2,000), 1.81 mg of (R$_a$,S)-DBT-Bn-SIPHOX (0.0023 mmol) and 10 ml of tetrahydrofuran. The formed yellow solution was stirred for 30 min at ambient temperature. Then, 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 24 ml of methanol, 6 ml of tetrahydrofuran and 0.12 ml of (S)-1-phenylethylamine (0.92 mmol) were added. The autoclave was sealed and the hydrogenation was run at 60° C. for 20 h and subsequently 80° C. for 2 h under 30 bar of hydrogen. After the autoclave was opened and the yellowish solution was rotary evaporated to dryness (50° C./5 mbar) to afford crude (R)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 98.5% (>99.9% conversion) and an enantiomeric purity of 99.5%.

Example 8.6

In a glove box (O$_2$ content≦2 ppm), a 185-ml stainless steel autoclave was charged with 1.14 mg of [Ir(COD)$_2$]BF$_4$ (0.0023 mmol, S/C 2'000), 1.99 mg of (R$_a$,S)-DBT-Bn-SIPHOX (0.0025 mmol) and 10 ml of tetrahydrofuran. The formed yellow solution was stirred for 30 min at ambient temperature. Then, 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 24 ml of methanol, 6 ml of tetrahydrofuran and 0.12 ml of (S)-1-phenylethylamine (0.92 mmol) were added. The autoclave was sealed and the hydrogenation was run at 60° C. for 20 h and subsequently 80° C. for 2 h under 30 bar of hydrogen. After the autoclave was opened and the yellowish solution was rotary evaporated to dryness (50° C./5 mbar) to afford crude (R)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 98.7% (>99.9% conversion) and an enantiomeric purity of 99.6%.

Example 8.7

In a glove box (O$_2$ content≦2 ppm), a 185-ml stainless steel autoclave was charged with 2.00 g of (Z)-2-methoxy-3-{4-[2-(5-methyl-2-phenyl-oxazol-4-yl)-ethoxy]-benzo[b]thiophen-7-yl}-acrylic acid (4.59 mmol), 1.80 mg of [Ir((S$_a$,R)-DBT-Bn-SIPHOX)(COD)]BF$_4$ (0.0015 mmol, S/C 3,000), 24 ml of methanol, 16 ml of tetrahydrofuran and 0.12 ml of (S)-1-phenylethylamine (0.92 mmol). The autoclave was sealed and the hydrogenation was run at 80° C. for 22 h under 30 bar of hydrogen. After the autoclave was opened and the yellowish solution was rotary evaporated evaporated to dryness (50° C./5 mbar) to afford crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 96.7% (99.9% conversion) and an enantiomeric purity of 99.5%.

Example 9

In an analogous manner to Example 4 the following hydrogenation was performed at 40° C. under 30 bar of hydrogen (reaction time: 16 h) using [Ir((S,S)-Xyl-Skewphos)(COD)]BF$_4$ (S/C 1,000) as catalysts to afford crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 98.8% (99.4% conversion) and an enantiomeric purity of 85%.

Example 10

In an analogous manner to Example 2 the following hydrogenation was performed at 60° C. under 30 bar of hydrogen (reaction time: 16 h) using [Ir((S,R,R)-Trifer)(COD)]BARF (S/C 250) as catalysts to afford crude (R)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 98.0% (>99.9% conversion) and an enantiomeric purity of 86%.

Example 11

In a glove box (O$_2$ content≦2 ppm), a 50-ml stainless steel autoclave was charged with 1.00 g of (Z)-2-methoxy-3-{4-[2-(5-methyl-2-phenyl-oxazol-4-yl)-ethoxy]-benzo[b]thiophen-7-yl}-acrylic acid (2.30 mmol), 1.99 mg of [Ru(η$^5$-2,4-DMP)((R)—(S)—PPF—PtBu$_2$)(NCMe)]BF$_4$ (0.0023 mmol, S/C 1,000), 12 ml of methanol, 8 ml of dichloromethane and 0.06 ml of (S)-1-phenylethylamine (0.47 mmol). The autoclave was sealed and the hydrogenation was run at 40° C. under 30 bar of hydrogen. After 16 h the autoclave was opened and the yellowish solution was rotary evaporated to dryness (50° C./5 mbar) to afford the crude (R)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 99.6% (>99.9% conversion) and an enantiomeric purity of 89%.

HPLC method for chemical purity (area-%, (S)-phenylethylamine not included): YMC-Pack Pro C18, 150×4.6 mm; mobile phase A: mobile phase A: water with 0.1% TFA, B: NCMe with 0.1% TFA, 22° C., 2 ml/min, isocratic A/B 51/49% during 10 min, gradient from 51/49% to 5/95% within 10 min and 5 min at 5/95%, 285 nm. Retention times: 11.2 min (S)- and (R)-2-methoxy-3-{4-[2-(5-methyl-2-phenyl-oxazol-4-yl)-ethoxy]-benzo[b]thiophen-7-yl}-propionic acid; 12.4 min (E)-2-methoxy-3-{4-[2-(5-methyl-2-phenyl-oxazol-4-yl)-ethoxy]-benzo[b]thiophen-7-yl}-acrylic acid; 14.0 min (Z)-2-methoxy-3-{4-[2-(5-methyl-2-phenyl-oxazol-4-yl)-ethoxy]-benzo[b]thiophen-7-yl}-acrylic acid.

HPLC method for ee determination (area-%): Chiralpak-ADH column, 25 cm×4.6 mm, 90% heptane/10% ethanol with 0.5% trifluoroacetic acid, flow 0.7 ml/min, 30° C., 270 nm. Retention times: 22.1 min (R)-2-methoxy-3-{4-[2-(5-methyl-2-phenyl-oxazol-4-yl)-ethoxy]-benzo[b]thiophen-7- yl}-propionic acid; 26.0 min (S)-2-methoxy-3-{4-[2-(5-methyl-2-phenyl-oxazol-4-yl)-ethoxy]-benzo[b]thiophen-7-yl}-propionic acid.

Examples 12.1-12.5

In an analogous manner to Example 11 the following hydrogenations were performed at 40° C. under 30 bar of hydrogen (reaction time: 16 h) using ruthenium complexes of general formula [Ru($\eta^5$-2,4-DMP)(Phosphorous Ligand)(NCMe)]BF$_4$ as catalysts to afford crude 2-methoxy-3-{4-[2-(5-methyl-2-phenyl-oxazol-4-yl)-ethoxy]-benzo[b]thiophen-7-yl}-propionic acid (Acid I) as listed in Table 3.

TABLE 3

| Exp. No. | Phosphorus Ligand | Conv. [%] | Acid I Purity [%] | Acid I Ee [%]/ Configuration |
|---|---|---|---|---|
| 12.1 | (R)-(R)-PPPhFCHCH$_3$—P(Norbornyl)$_2$ | >99.9 | 97.1 | 69/S |
| 12.2 | (R)-(R)-Cy$_2$PPhFCH—CH$_3$P(3,5-CF$_3$Ph)$_2$ | >99.9 | 99.4 | 79/S |
| 12.3 | (R)-(S)-NMe$_2$—PPh$_2$-Mandyphos | 99.6 | 99.1 | 69/S |
| 12.4 | (R)-(S)-NMe$_2$—P(3,5-Me-4-MeOPh)$_2$-Mandyphos | 99.3 | 98.8 | 70/S |
| 12.5 | (R)-(R)-PPPhFCHCH$_3$—P(3,5-CF$_3$Ph)$_2$ | >99.9 | 99.6 | 58/R |

Example 13

In an analogous manner to Example 11 the following hydrogenations were performed at 40° C. under 30 bar of hydrogen (reaction time: 16 h) using ruthenium complex [RuI($\eta^5$-2,4-DMP)((S)—(R)—PPPhCHNMe$_2$F—PP)] as catalysts to afford crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 98.7% (99.2% conversion) and an enantiomeric purity of 46%.

Example 14

In a glove box (O$_2$ content≦2 ppm), a 50-ml stainless steel autoclave was charged with 2.26 mg of [Ru($\eta^5$-2,4-DMP)((S)—(R)-(3,5-Me$_2$-4-MeOPh)$_2$PF—PtBu$_2$)(NCMe)]BF$_4$ (0.0023 mmol, S/C 1,000) and 6 ml of dichloromethane. The resulting violet solution was stirred for 2 h at r.t. Then, 1.00 g of (Z)-2-methoxy-3-{4-[2-(5-methyl-2-phenyl-oxazol-4-yl)-ethoxy]-benzo[b]thiophen-7-yl}-acrylic acid (2.30 mmol), 4 ml of dichloromethane, 10 ml of THF and 0.06 ml of (S)-1-phenylethylamine (0.47 mmol) were added. The autoclave was sealed and the hydrogenation was run under stirring at 40° C. under 30 bar of hydrogen. After 16 h the autoclave was opened and the yellowish solution was rotary evaporated to dryness (50° C./5 mbar) to afford the crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 99.5% (>99.9% conversion) and an enantiomeric purity of 87%.

Example 15

In an analogous manner to Example 14 the following hydrogenations were performed at 40° C. under 30 bar of hydrogen (reaction time: 16 h) using ruthenium complex [Ru(5-2,4-DMP)((S)—(R)-2-Fur2 PF—PtBu2)(NCMe)]BF4 as catalysts to afford crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 99.3% (>99.9% conversion) and an enantiomeric purity of 73%.

Example 16

In a glove box (O$_2$ content≦2 ppm), a 50-ml stainless steel autoclave was charged with 1.99 mg of [Ru($\eta^5$-2,4-DMP)((R)—(S)—PPF—PtBu$_2$)(NCMe)]BF$_4$ (0.0023 mmol, S/C 1,000) and 5 ml of dichloromethane. The resulting violet solution was stirred for 2 h at r.t. Then, 1.00 g of (Z)-2-methoxy-3-{4-[2-(5-methyl-2-phenyl-oxazol-4-yl)-ethoxy]-benzo[b]thiophen-7-yl}-acrylic acid (2.30 mmol), 2.5 ml of dichloromethane, 7.5 ml of THF and 0.06 ml of (S)-1-phenylethylamine (0.47 mmol) were added. The autoclave was sealed and the hydrogenation was run under stirring at 40° C. under 30 bar of hydrogen. After 16 h the autoclave was opened and the yellowish solution was rotary evaporated to dryness (50° C./5 mbar) to afford (R)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 99.2% (>99.9% conversion) and an enantiomeric purity of 90%.

Examples 17.1-17.2

In an analogous manner to Example 16 the following hydrogenations were performed at 40° C. under 30 bar of hydrogen (reaction time: 16 h) using ruthenium complexes of general formula [Ru($\eta^5$-2,4-DMP)(Phosphorus Ligand)(NCMe)]BF$_4$ as catalysts to afford crude 2-methoxy-3-{4-[2-(5-methyl-2-phenyl-oxazol-4-yl)-ethoxy]-benzo[b]thiophen-7-yl}-propionic acid (Acid I) as listed in Table 4.

TABLE 4

| Exp. No. | Phosphorus Ligand | Conv. [%] | Acid I Purity [%] | Acid I Ee [%]/ Configuration |
|---|---|---|---|---|
| 17.1 | (S)-(R)-Cy$_2$PF—PtBu$_2$ | 98.7 | 98.6 | 74/S |
| 17.2 | (S)-(R)-(4-CF$_3$Ph)$_2$PF—PtBu$_2$ | 99.9 | 99.6 | 84/S |

Example 18

In a glove box (O$_2$ content≦2 ppm), a 50-ml stainless steel autoclave was charged with 0.66 mg of [Ru($\eta^5$-2,4-DMP)((R)—(S)—PPF—PtBu$_2$)(NCMe)]BF$_4$ (0.0008 mmol, S/C 3,000) and 5 ml of dichloromethane. The resulting violet solution was stirred for 2 h at r.t. Then, 1.00 g of (Z)-2-methoxy-3-{4-[2-(5-methyl-2-phenyl-oxazol-4-yl)-ethoxy]-benzo[b]thiophen-7-yl}-acrylic acid (2.30 mmol), 2.5 ml of dichloromethane, 7.5 ml of THF and 0.06 ml of (S)-1-phenylethylamine (0.47 mmol) were added. The autoclave was sealed and the hydrogenation was run under stirring at 40° C. under 30 bar of hydrogen. After 16 h the autoclave was opened and the yellowish solution was rotary evaporated to dryness (50° C./5 mbar) to afford (R)-2-methoxy-3-{4-[2-(5-methyl-2-phenyl-oxazol-4-yl)-ethoxy]-benzo[b]thiophen-7- yl}-propionic acid (Acid I) as a white solid with a chemical purity of 99.5% (99.9% conversion) and an enantiomeric purity of 89%.

Example 19

In a glove box (O₂ content≦2 ppm), a 50-ml stainless steel autoclave was charged with 0.66 mg of [Ru(η⁵-2,4-DMP)((R)—(S)—PPF—PtBu₂)(NCMe)]BF₄ (0.0008 mmol, S/C 3,000) and 5 ml of dichloromethane. The resulting violet solution was stirred for 2 h at r.t. Then, 1.00 g of (Z)-2-methoxy-3-{4-[2-(5-methyl-2-phenyl-oxazol-4-yl)-ethoxy]-benzo[b]thiophen-7-yl}-acrylic acid (2.30 mmol), 10 ml of dichloromethane and 0.06 ml of (S)-1-phenylethylamine (0.47 mmol) were added. The autoclave was sealed and the hydrogenation was run under stirring at 40° C. under 30 bar of hydrogen. After 16 h the autoclave was opened and the yellowish solution was rotary evaporated to dryness (50° C./5 mbar) to afford (R)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 99.5% (99.9% conversion) and an enantiomeric purity of 90%.

Comparative Example A

In a glove box (O₂ content≦2 ppm), a 50-ml stainless steel autoclave was charged with 0.62 mg of [Ru(OAc)₂((S)-TMBTP)] (0.0008 mmol, S/C 3'000) (prepared according to EP 1,670,792 B1; TMBTP=2,2',5,5'-Tetramethyl-4,4'-bis (diphenylphosphino)-3,3'-bithiophene) and 5 ml of methanol. The resulting orange solution was stirred for 2 h at r.t. Then, 1.00 g of (Z)-2-methoxy-3-{4-[2-(5-methyl-2-phenyl-oxazol-4-yl)-ethoxy]-benzo[b]thiophen-7-yl}-acrylic acid (2.30 mmol), 4 ml of methanol, 6 ml of THF and 0.06 ml of (S)-1-phenylethylamine (0.47 mmol) were added. The autoclave was sealed and the hydrogenation was run under stirring at 40° C. under 30 bar of hydrogen. After 16 h the autoclave was opened and the yellowish solution was rotary evaporated to dryness (50° C./5 mbar) to afford crude (S)-2-methoxy-3-{4-[2-(5-methyl-2-phenyl-oxazol-4-yl)-ethoxy]-benzo[b]thiophen-7-yl}-propionic acid (Acid I) as a white solid with a chemical purity of 99.7% (99.9% conversion) and an enantiomeric purity of 89%.

The invention claimed is:

1. A process for the preparation of a compound of formula (I)

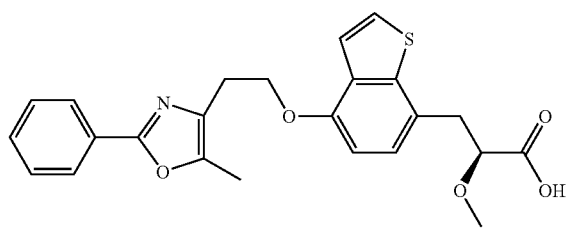

(I)

or a salt thereof, wherein a compound of formula (II)

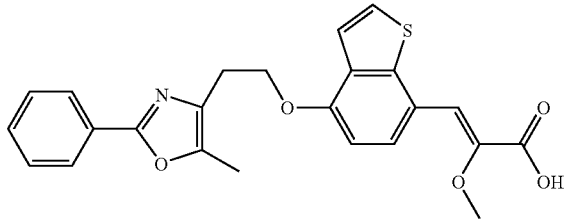

(II)

or a salt thereof is hydrogenated in the presence of a catalyst which comprises iridium and a compound of formula (X)

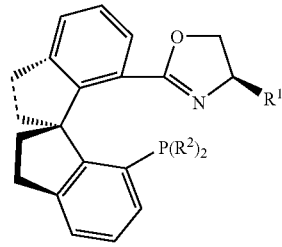

(X)

wherein:
R¹ is benzyl, and
R² is 3,5-di-tert-butylphenyl.

2. A process according to claim 1 wherein the catalyst is Ir(L¹)(L²)ₙY wherein:
Ir is iridium;
L¹ is (Sₐ,R)-7-[4,5-Dihydro-4-benzyloxazol-2-yl]-7'-di(3,5-di-tert-butylphenyl) phosphino-1,1'-spirobiindane;
L² is selected from the group consisting of: cyclooctene, 1,5-cyclooctadiene, ethylene, 1,5-hexadiene and norbornadiene;
Y is selected from the group consisting of: chloride, iodide, bromide, fluoride, trifluoroacetate, tetrafluoroborate, tetrakis[3,5-bis(trifluoromethyl)phenyl]borate, tetraphenylborate, hexafluoroantimonate, hexafluorophosphate, triflate, mesylate, perchlorate, perbromate, periodate, nitrate, hydrogen sulfate and acetylacetonate; and
n is 1 or 2.

3. A process according to claim 2, wherein the catalyst is selected from the group consisting of:
[Ir((Sₐ,R)-7-[4,5-dihydro-4-benzyloxazol-2-yl]-7'-di(3,5-di-tert-butylphenyl)phosphino-1,1'-spirobiindane)(1,5-cyclooctadiene)][tetrakis[3,5-bis(trifluoromethyl)phenyl]borate];
[Ir((Sₐ,R)-7-[4,5-dihydro-4-benzyloxazol-2-yl]-7'-di(3,5-di-tert-butylphenyl)phosphino-1,1'-spirobiindane)(1,5-cyclooctadiene)][tetrafluoroborate];
[Ir((Sₐ,R)-7-[4,5-dihydro-4-benzyloxazol-2-yl]-7'-di(3,5-di-tert-butylphenyl)phosphino-1,1'-spirobiindane)(1,5-cyclooctadiene)][trifluoromethanesulfonate]; and
[Ir((Sₐ,R)-7-[4,5-dihydro-4-benzyloxazol-2-yl]-7'-di(3,5-di-tert-butylphenyl) phosphino-1,1'-spirobiindane)(1,5-cyclooctadiene)][chloride].

* * * * *